United States Patent
Riondel et al.

(10) Patent No.: US 6,521,782 B1
(45) Date of Patent: Feb. 18, 2003

(54) METHOD FOR MAKING AQUEOUS SOLUTIONS OF UNSATURATED QUATERNARY AMMONIUM SALTS

(75) Inventors: Alain Riondel, Forbach (FR); Gilles Herbst, Spichern (FR); Marc Esch, Freyming-Meriebach (FR); Eric Delaunay, Rebigue (FR); Peter Meyer, Paris (FR)

(73) Assignee: Atofina (FR)

( * ) Notice: Subject to any disclaimer, the term of this patent is extended or adjusted under 35 U.S.C. 154(b) by 0 days.

(21) Appl. No.: 09/889,727

(22) PCT Filed: Jan. 20, 2000

(86) PCT No.: PCT/FR00/00122
§ 371 (c)(1), (2), (4) Date: Sep. 27, 2001

(87) PCT Pub. No.: WO00/43346
PCT Pub. Date: Jul. 27, 2000

(30) Foreign Application Priority Data

Jan. 21, 1999 (FR) .............................................. 99/00641

(51) Int. Cl.⁷ .............................................. C07C 69/52
(52) U.S. Cl. ........................ 560/222; 564/288; 564/296
(58) Field of Search ................................ 560/222, 288, 560/296; 564/288, 296

(56) References Cited

U.S. PATENT DOCUMENTS

| | | | | |
|---|---|---|---|---|
| 3,872,138 A | * | 3/1975 | Ogata .......................... | 260/404 |
| 4,169,208 A | * | 9/1979 | Kametani et al. ........... | 560/222 |
| 4,362,890 A | * | 12/1982 | Ohshima et al. ............ | 560/222 |
| 4,745,214 A | * | 5/1988 | Hess et al. .................. | 560/222 |
| 5,260,480 A | * | 11/1993 | Lacroix et al. ............. | 560/222 |

FOREIGN PATENT DOCUMENTS

| | | |
|---|---|---|
| EP | 250325 | 12/1987 |
| EP | 329512 | 8/1989 |
| EP | 818437 | 1/1998 |
| EP | 819671 | 1/1998 |
| WO | 89/07588 | 8/1989 |

* cited by examiner

*Primary Examiner*—Brian Davis
(74) *Attorney, Agent, or Firm*—Millen, White, Zelano & Branigan, P.C.

(57) ABSTRACT

The present invention relates to a process for the manufacture of aqueous solutions of unsaturated quaternary ammonium salts. The salts can correspond to the following formula (I):

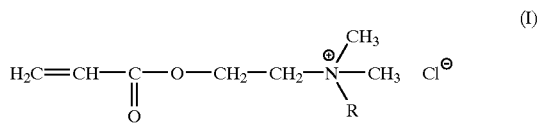

in which R represents a methyl or benzyl radical, by reaction, in the presence of water, of N,N-dimethyl-amninoethyl acrylate (DAMEA) with a quaternizing agent of formula (II):

R—Cl (II)

in which R is as defined above. Generally, the reaction is carried out in a closed reactor, which includes all the DAMEA and has been pressurized by air or depleted air to 0.5 to 3 bar, by continuously introducing, at a temperature of 35 to 65° C., the quatenlizing agent (II) and the water, until a concentration of salt (I) in the water is obtained. The water starts to be introduced beginning when 0–20% of the amount by weight of the quaternizing agent (II) necessary for the reaction has been added and it being possible for the pressure at the end of the reaction to reach 9 bar. Next, the reactor can be depressurized while keeping the oxygen content constant by simultaneous introduction of air and, after returning to atmospheric pressure, the residual quaternizing agent may be removed.

15 Claims, No Drawings

METHOD FOR MAKING AQUEOUS SOLUTIONS OF UNSATURATED QUATERNARY AMMONIUM SALTS

The present invention relates to the manufacture of aqueous solutions of unsaturated quaternary ammonium salts (hereinafter denoted quaternary salts) corresponding to the following formula (I):

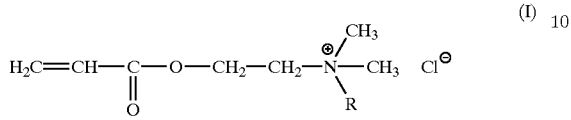

in which R represents a methyl or benzyl radical, by reaction, in the presence of water, of N,N-dimethylaminoethyl acrylate (DAMEA) with a quaternizing agent of formula (II):

R—Cl (II)

in which R is as defined above.

Aqueous solutions of quaternary salts (I) are used to prepare polymers intended to act as cationic flocculents in water treatment.

European patent EP-B-250 325 discloses a process for the preparation of aqueous solutions of quaternary salts, including those of formula (I), according to which process, in the presence of at least one polymerization inhibitor:

in a first stage (a), DAMEA is reacted with 5 to 20% by weight of the amount by weight of the quaternizing agent necessary for the reaction or, according to an alternative form (a'), with 5 to 20% by weight, with respect to the weight of the DAMEA, of an aqueous solution of quaternary salts, which solution comprises from 50 to 85% by weight of quaternary salts; and in a second stage (b), the water and the quaternizing agent are continuously added until the desired concentration of quaternary salts in the water is obtained.

During stages (a) and (b), the temperature is maintained at a value of between 30 and 60° C. Furthermore, during stages (a) and (b) and in particular near the end of the reaction, a stream of oxygenated gas is maintained in the reaction medium such that the ratio by volume (or volumetric throughput) of total gas at the outlet of the reactor to the volume (or volumetric throughput) of oxygen introduced at the inlet of this same reactor is less than 100.

This process makes it possible to prepare aqueous solutions of quaternary salts which have a stability at ambient temperature of greater than one year. However, a particularly high content of impurities, in particular of

and of DAMEA, is found in these solutions. In addition, this process requires relatively long reaction times, which represents an obvious economic disadvantage.

A process intended to reduce the formation of the impurities during the quaternization reaction was then provided in international application WO 89/07 588. In accordance with this process, the reaction is carried out at a temperature of between 10 and 80° C., and (a) in a first stage, all or a portion of the quaternizing agent necessary for the reaction is introduced into the reactor, this agent being in the liquid state under the reaction conditions, (b) subsequently, the DAMEA is added, and (c) as soon as 0 to 30% of the stoichiometry of the DAMEA has been introduced into the reactor, the remainder of the quaternizing agent, the remainder of the DAMEA and the water are continuously and simultaneously added until the desired concentration of quaternary salts is obtained, (d) and, in the case where the quaternizing agent is introduced in the gaseous state at the reaction temperature, the reaction is carried out in the presence of oxygen and a pressure is applied so that the quaternizing agent is liquid at the reaction temperature and, at the end of the reaction, the pressure is gradually decreased to atmospheric pressure and, simultaneously, a ratio as volumetric throughput of total gas at the outlet of the reactor to the volumetric throughput of oxygen introduced into the reactor of less than 100 is imposed.

The above process according to WO 89/07 588 introduces significant improvements to the process, according to EP-B-250 325. However, it transpired that the purity with which the quaternary salts are obtained is still insufficient. Thus, during the reaction of DAMEA with $CH_3Cl$ in an aqueous medium, resulting in the salt also denoted subsequently by the abbreviation ADAMQUAT MC, the dimer of ADAMQUAT MC, represented by the formula (1):

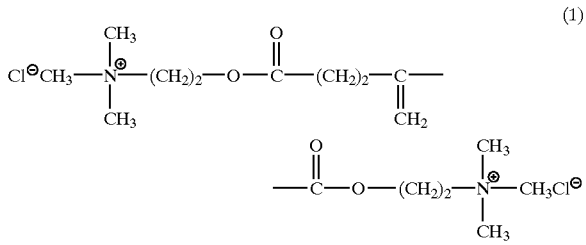

is formed as impurities, in addition to acrylic acid (AA), formed by hydrolysis of DAMEA.

By virtue of a series of tests of reactivity with respect to polymerization, it was possible to demonstrate that these impurities affected the quality of the cationic polymers derived from the ADAMQUAT.

The applicant company has thus looked for operating conditions for the preparation of aqueous solutions of the salt of formula (I) which are capable of minimizing the abovementioned impurities, so as to provide a salt (I) in aqueous solution of very high analytical quality.

This novel process, which thus forms the subject matter of the present invention, is characterized in that:

(a) the reaction is carried out in a closed reactor, which comprises all the DAMEA and which has been pressurized by air or depleted air to 0.5 to 3 bar, by continuously introducing, at a temperature of 35 to 65° C., in particular of 40 to 60° C., on the one hand, the quaternizing agent (II) and, on the other hand, the water, until the desired concentration of salt (I) in the water is obtained, the start of the introduction of the water beginning when 0–20%, in particular 5–15%, of the amount by weight of the quaternizing agent (II) necessary for the reaction has been added and it being possible for the pressure at the end of the reaction to reach 9 bar, in particular 4 to 7 bar; then (b) the reactor is depressurized while keeping the oxygen content constant by simultaneous introduction of air and, after returning to atmospheric pressure, the residual quaternizing agent is removed, for example by stripping with air.

In accordance with other specific characteristics of the process according to the invention:

the quaternizing agent is introduced over a period of time of 1–7 hours and the water over a period of time of 2–8 hours;

the reaction is carried out with a molar ratio of the quaternizing agent to the DAMEA of 1 to 1.1, preferably of 1 to 1.05;

the reaction is carried out with a mean ratio of water/quaternizing agent throughput of 0.1–1.2, in particular of 0.3–0.8.

The process according to the invention makes it possible in particular to prepare aqueous solutions having a concentration of quaternary salts (I) of 50 to 85% by weight and comprising very low amounts of impurities, as illustrated in Table 1 below.

Furthermore, the process according to the present invention can be carried out in the presence of at least one stabilizer, which can be chosen from 3,5-di(tert-butyl)-4-hydroxytoluene, hydroquinone methyl ether, hydroquinone, catechol, tert-butylcatechol, phenothiazine and the mixtures of these stabilizers, the content of stabilizing agent(s) being in particular from 20 to 2000 ppm, preferably from 100 to 1200 ppm, with respect to the aqueous solution of quaternary salt (I).

In addition, it is possible to add, to the reaction medium, at least one sequestering agent for metals chosen in particular from diethylenetriamine-pentaacetic acid, the pentasodium salt of diethylene-triaminepentaacetic acid, N-(hydroxyethyl)ethylene-diaminetriacetic acid and the trisodium salt of N-(hydroxyethyl)ethylene-diaminetriacetic acid, the content of sequestering agent(s) being in particular from 1 to 100 ppm, preferably from 5 to 30 ppm, with respect to the aqueous solution of quaternary salt (I).

Generally, the sequestering agents are added in the form of an aqueous solution, as they are generally available in this form. Thus, the pentasodium salt of diethylenetriaminepentaacetic acid sold under the name Versenex 80 is provided in the form of an approximately 40% by weight aqueous solution.

The following examples illustrate the present invention without, however, limiting the scope thereof. From these examples, the percentages are by weight, unless otherwise indicated.

EXAMPLE 1:

429 g of DAMEA were charged to a 1l jacketed glass reactor, specially designed to withstand pressure, equipped with a temperature probe, with a gas/liquid specific stirrer (turbine with a hollow shaft), with a valve tared at 10 bar, with a bursting disc and with dip pipes for the introduction of the various reactants. The reactor was closed and then pressurized with 1 bar of depleted air. Stirring and heating were begun.

As soon as the temperature reached 40° C. (set temperature: 47° C.), introduction of $CH_3Cl$ was begun at the rate of 159 g/h. As soon as 15 g of $CH_3Cl$, i.e. 10% of the $CH_3Cl$ stoichiometry, were added, the introduction of water was started at a throughput of 60 g/h while maintaining the addition of $CH_3Cl$. The ratio of $H_2O/CH_3Cl$ throughput was kept constant at 0.37 throughout the reaction. When all the water was introduced (i.e. 143 g), the reactor was brought back to atmospheric pressure by using the following protocol:

degassing the excess $CH_3Cl$ for 30 minutes with simultaneous introduction of air into the charge (throughput: 3 Sl/h);

gradual return to atmospheric pressure.

The traces of $CH_3Cl$ was subsequently removed by stripping with air (throughput: 5 Sl/h) for 30 minutes. The reactor was subsequently cooled and then emptied.

The crude reaction mixture (716 g) was analyzed by high performance liquid chromatography (HPLC) to determine the contents of acrylic acid and of compound (1). The results are presented in Table 1.

The durations of the various phases of the reaction were as follows:

| | |
|---|---|
| $CH_3Cl$ introduction | 1 h |
| $H_2O$ introduction | 2.3 h |
| degassing | 0.5 h |
| stripping | 0.5 h | i.e. a total duration of approximately 3.5 h.

EXAMPLES 2 to 4:

The preparation was carried out as in Example 1, except that the $CH_3Cl$ throughput was varied. The results are presented in Table 1.

EXAMPLES 5 to 7

The preparation was carried out as in Example 3, except that the introduction of the water was begun from the beginning.

EXAMPLES 8 to 10

The preparation was carried out as in Example 3, except that the temperature was varied.

The results are presented in Table 1.

TABLE 1

[$CH_3Cl$]/[DAMEA] = 1.05; Maximum pressure: 6 bar; DAMEA: 429 g (3 mol); $CH_3Cl$ = 159.1 g (3.15 mol)

| Example | Mass of the crude reaction mixture (g) | Duration of introduction of $CH_3Cl$ (h) | T (° C.) | Mean ratio of $H_2O/CH_3Cl$ throughput | HPLC anaylsis (ppm) | | |
|---|---|---|---|---|---|---|---|
| | | | | | AA** | ADAMQUAT MC dimer of formula (1)*** | ADAMQUAT MC (%)**** |
| 1 | 716 | 1 | 47 | 0.37 | 267 | 125 | 81.8 |
| 2 | 716.5 | 2.25 | 47 | 0.7 | 810 | 397 | 80 |
| 3 | 699 | 4 | 47 | 0.85 | 990 | 1 070 | 81.1 |
| 4 | 706 | 7.25 | 47 | 0.66 | 892 | 2 145 | 80.2 |
| 5* | 717.5 | 4 | 47 | 0.5 then 0.7 at mid-reaction | 769 | 727 | |

TABLE 1-continued

[CH₃Cl]/[DAMEA] = 1.05; Maximum pressure: 6 bar; DAMEA: 429 g (3 mol); CH₃Cl = 159.1 g (3.15 mol)

| Example | Mass of the crude reaction mixture (g) | Duration of introduction of CH₃Cl (h) | T (° C.) | Mean ratio of H₂O/CH₃Cl throughput | HPLC anaylsis (ppm) | | |
|---|---|---|---|---|---|---|---|
| | | | | | AA** | ADAMQUAT MC dimer of formula (1)*** | ADAMQUAT MC (%)**** |
| 6* | 723.5 | 4 | 47 | 0.55 | 559 | 649 | |
| 7* | 691.5 | 4 | 47 | 0.38 then 0.55 at mid-reaction | 561 | 698 | |
| 8 | 680 | 4 | 30 | 0.76 | 6 259 | 12 004 | 75 |
| 9 | 685.5 | 4 | 40 | 0.64 | 597 | 410 | 81.2 |
| 10 | 708.5 | 4 | 58 | 0.6 | 540 | 1 360 | 78.9 |

*Introduction of the water from the beginning of the reaction
**AA = acrylic acid
***Content of ADAMQUAT MC dimer of formula (1), expressed arbitrarily as AA
****ADAMQUAT MC = aqueous solution of acryloyloxyethyltrimethylammonium chloride

What is claimed is:

1. A process for the manufacture of aqueous solutions of unsaturated quaternary ammonium salts corresponding to the following formula (I):

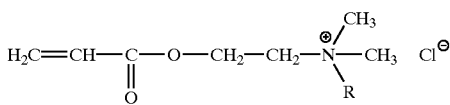

in which R represents a methyl or benzyl radical, by reaction, in the presence of water, of N,N-dimethylaminoethyl acrylate (DAMEA) with a quaternizing agent of formula (II):

in which R is as defined above, (a) the reaction is carried out in a closed reactor, which comprises all the DAMEA and which has been pressurized by air or depleted air to 0.5 to 3 bar, by continuously introducing, at a temperature of 35 to 65° C., the quaternizing agent (II) and the water, until a concentration of salt (I) in the water is obtained, the start of the introduction of the water beginning when 0–20% of the amount by weight of the quaternizing agent (II) necessary for the reaction has been added and it being possible for the pressure at the end of the reaction to reach 9 bar; then (b) the reactor is depressurized while keeping the oxygen content constant by simultaneous introduction of air and, after returning to atmospheric pressure, the residual quaternizing agent is removed.

2. The process as claimed in claim 1, wherein the reaction is carried out at a temperature of 40 to 60° C.

3. The process as claimed in claim 1, wherein the reaction is carried out with a pressure which, at the end of the reaction, reaches 4 to 7 bar.

4. The process as claimed in claim 1, wherein the introduction of the water is started when 5–15% of the amount by weight of the quaternizing agent (II) necessary for the reaction has been added.

5. The process as claimed in claim 1, wherein the quaternizing agent is introduced over a period of time of 1–7 hours and the water is introduced over a period of time of 2–8 hours.

6. The process as claimed in claim 1, wherein the reaction is carried out with a molar ratio of the quaternizing agent to the DAMEA of 1 to 1.1.

7. The process according to claim 1, wherein the reaction is carried out with a mean ratio of water/quaternizing agent throughput of 0.1–1.2.

8. The process as claimed in claim 1, resulting in an aqueous solution having a concentration of quaternary salts (I) of 50 to 85% by weight.

9. The process as claimed in claim 1 carried out in the presence of at least one stabilizer which is 3,5-di(tert-butyl)-4-hydroxytoluene, hydroquinone methyl ether, hydroquinone, catechol, tert-butylcatechol, phenothiazine or mixtures of these stabilizers, the content of stabilizing agent(s) being from 20 to 2000 ppm with respect to the aqueous solution of quaternary salt (I).

10. The process as claimed in claim 9, carried out in the presence in addition of at least one sequestering agent for metals which is diethylene-triaminepentaacetic acid, the pentasodium salt of diethylenetriaminepentaacetic acid, N-(hydroxyethyl)-ethylenediaminetriacetic acid or the trisodium salt of N-(hydroxyethyl)ethylenediaminetriacetic acid, the content of sequestering agent(s) being 1 to 100 ppm, with respect to the aqueous solution of quaternary salt (I).

11. The process as claimed in claim 1, wherein residual quaternizing agent is removed by stripping with air.

12. The process as claimed in claim 1, wherein the reaction is carried out with a molar ratio of the quaternizing agent to the DAMEA of 1 to 1.05.

13. The process according to claim 1, wherein the reaction is carried out with a mean ratio of water/quaternizing agent throughput of 0.3–0.8.

14. The process as claimed in claim 1 carried out in the presence of at least one stabilizer which is 3,5-di(tert-butyl)-4-hydroxytoluene, hydroquinone methyl ether, hydroquinone, catechol, tert-butylcatechol, phenothiazine or mixtures of these stabilizers, the content of stabilizing agent(s) being 100 to 1200 ppm, with respect to the aqueous solution of quaternary salt (I).

15. The process as claimed in claim 9, carried out in the presence in addition of at least one sequestering agent for metals which is diethylene-triaminepentaacetic acid, the pentasodium salt of diethylenetriaminepentaacetic acid, N-(hydroxyethyl)-ethylenediaminetriacetic acid or the trisodium salt of N-(hydroxyethyl)ethylenediaminetriacetic acid, the content of sequestering agent(s) being 5 to 30 ppm, with respect to the aqueous solution of quaternary salt (I).

* * * * *